United States Patent
Oberdörfer et al.

(10) Patent No.: US 8,453,509 B2
(45) Date of Patent: *Jun. 4, 2013

(54) METHOD FOR THE NON-DESTRUCTIVE TESTING OF A TEST OBJECT BY WAY OF ULTRASOUND AND APPARATUS THEREFOR

(75) Inventors: York Oberdörfer, Köln (DE); Wolf-Dietrich Kleinert, Bonn (DE)

(73) Assignee: GE Sensing & Inspection Technologies GmbH (DE)

( * ) Notice: Subject to any disclaimer, the term of this patent is extended or adjusted under 35 U.S.C. 154(b) by 240 days.

This patent is subject to a terminal disclaimer.

(21) Appl. No.: 12/811,558

(22) PCT Filed: Dec. 23, 2008

(86) PCT No.: PCT/EP2008/068236
§ 371 (c)(1),
(2), (4) Date: Sep. 23, 2010

(87) PCT Pub. No.: WO2009/087065
PCT Pub. Date: Jul. 16, 2009

(65) Prior Publication Data
US 2011/0016979 A1 Jan. 27, 2011

(30) Foreign Application Priority Data

| | | |
|---|---|---|
| Jan. 4, 2008 | (DE) | 10 2008 003 257 |
| Apr. 11, 2008 | (DE) | 10 2008 018 648 |
| Apr. 18, 2008 | (DE) | 10 2008 019 778 |
| Jun. 16, 2008 | (DE) | 10 2008 002 445 |

(51) Int. Cl.
*G01N 29/00* (2006.01)
(52) U.S. Cl.
USPC .......................................................... 73/632
(58) Field of Classification Search
USPC ..................... 73/623, 632, 598, 627, 629
See application file for complete search history.

(56) References Cited

U.S. PATENT DOCUMENTS

| | | | |
|---|---|---|---|
| 4,111,557 A | 9/1978 | Rottenkolber et al. | |
| 5,511,425 A | 4/1996 | Kleinert et al. | |

(Continued)

FOREIGN PATENT DOCUMENTS

| | | |
|---|---|---|
| DE | 2335567 A1 | 2/1975 |
| DE | 2901818 A1 | 7/1980 |
| WO | WO2007144271 | 12/2007 |

OTHER PUBLICATIONS

International Search Report PCT/EP2008/068236; Dated May 25, 2009.

(Continued)

*Primary Examiner* — Jewel V Thompson
(74) *Attorney, Agent, or Firm* — Cantor Colburn LLP

(57) ABSTRACT

A method for the non-destructive testing of a test specimen by means of ultrasound and a corresponding device, the method including insonification of directed ultrasonic pulses into the test specimen 100 at an insonification angle β, wherein the insonification angle β is adjusted electronically, a. recording echo signals that result from the ultrasonic pulses insonified into the test specimen 100, b. calculation of an ERS value of a flaw 102 in the volume of the test specimen from echo signals that can be assigned to the flaw 102 for a plurality of insonification angles β, and c. generation of a graphic representation of the flaw 102, from which the dependence of the calculated ERS values of the flaw on the insonification value βcan be read off at least qualitatively.

19 Claims, 5 Drawing Sheets

U.S. PATENT DOCUMENTS

| | | | |
|---|---|---|---|
| 6,993,972 | B2 | 2/2006 | Basir et al. |
| 7,204,129 | B2 | 4/2007 | Basir et al. |
| 8,127,612 | B2 * | 3/2012 | Mitchell ............... 73/623 |
| 2006/0219013 | A1 | 10/2006 | Baba |
| 2006/0241456 | A1 | 10/2006 | Karasawa |
| 2011/0016978 | A1 * | 1/2011 | Kleinert et al. ............ 73/629 |
| 2011/0016979 | A1 | 1/2011 | Oberdorfer et al. |
| 2012/0024067 | A1 | 2/2012 | Oberdoerfer et al. |
| 2012/0095346 | A1 | 4/2012 | Yoshizawa et al. |
| 2012/0099397 | A1 | 4/2012 | Inoue et al. |

OTHER PUBLICATIONS

Deutsch V. et al.: "3.4 Fehlernachweis und Geratejustierung" Ultraschallpruefung: Grandlagen Und Industrielle Anwendungen, XX, XX, Jan. 1, 1997, pp. 80-133, p. 107, XP002280036.

International Search Report, PCT/EP2008/067044, Dated Mar. 20, 2009, European Patent Office.

International Search Report, PCT/EP2009/054102; dat of Mailing Oct. 5, 2009, European Patent Office.

Olympus, "Olympus NDT Introduces a Manual Weld Inspection Solution That Includes conventional UT and Phased Array", http://www.ndt.net/search, Waltham MA, Apr. 23, 2008, NDT.net Issue: 2008-05, p. 1.

Olympus, "Phased Array Probe Update" Weld Probe Series (WPS), Innovation in NDT, 920-143A-EN, www.olympusNDT.com, PA_Probe_Update_WPS_EN_0804, Canada, 2006, pp. 1-2.

Olympus, "Phased Array Probe Update" AWS and DGS Probes, Innovation in NDT 920-144A-EN, www.olympusNDT.com, PA_Probe_Update_DGS-AWS_EN_0804, Canada, 2006 Olympus NDT, pp. 1-2.

Olympus, "Ultrasound, UT Phased Array, Eddy Current, and EC Array" OmniScan MX, Innovation in NDT 920-061E, OmniScan_MX_EN_0611, Canada, 2003-2006 Olympus NDT, www.olympusNDT.com, pp. 1-14.

Olympus, "Entry-Level Manual Phased Array Solutions", OmniScan M, Innovation in NDT 930-168, www.olympusNDT.com, OmniScanM_EN_0712, Canada, 2006 Olympus NDT, pp. 1-2.

Olympus, "Phased Array Ultrasound Probe Catalog" Innovation in NDT, www.olympustNDT.com, Fourth Edition, Nov. 2006, PA_Probe_Catalog_EN_0611, Canada, 2003-2006 Olympus NDT, pp. 1-24.

Olympus, "Manual Weld Inspection Solution" Convential and Phased Array UT, Innovation in NDT 920-135A-EN, www.olympusNDT.com, OmniScan_Manual_Weld_EN_0804, Canada, 2008 Olymput NDT, pp. 1-3.

RD Tech, "Phased-Array Ultrasound Probe Catalog 2005-2006", Third edition, May 2005, PA_Probe_Catalog_9505, Canada, 2004-2005 R/D Tech Inc., www.rd-tech.com, 1-24.

Olympus, "New Bei Olympus NDT: Ultraschallbilder Mittels Phased Array—Die Neuen Ultraschallprufgerate der EPOCH 1000 Serie", http://www.olympus.at/corporate/1696_3065.htm, Jan. 1, 2009, Hamburg, Januar 2009, pp. 1-3.

RD Tech, "Ultrasound Phased-Array Transducer Catalog 2004-2005", R/D Tech Ultrasonic Transducers, Canada, 2004 by R/D Tech Inc., pp. 1-11.

RD Tech, "Innovation in NDT" Nondestructive Testing, Panametrics-NDT, A business of D/D Tech Instrumnets Inc., NDT engineering corporation, R/D Tech Inc. Aug. 2004, pp. 1-15.

RD Tech, "Ultrasound Phased-Array Probe Catalog 2003-2004" www.rd-tech.com, First edition, Nov. 2003, PA_Probe_Catalog 1103, Canada, 2003, R/D Tech Inc., pp. 1-18.

* cited by examiner

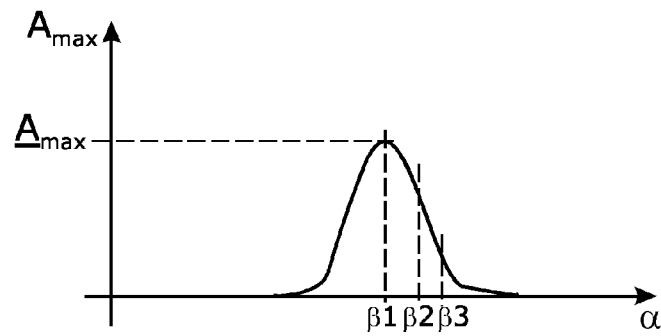
Fig. 3
Fig. 4
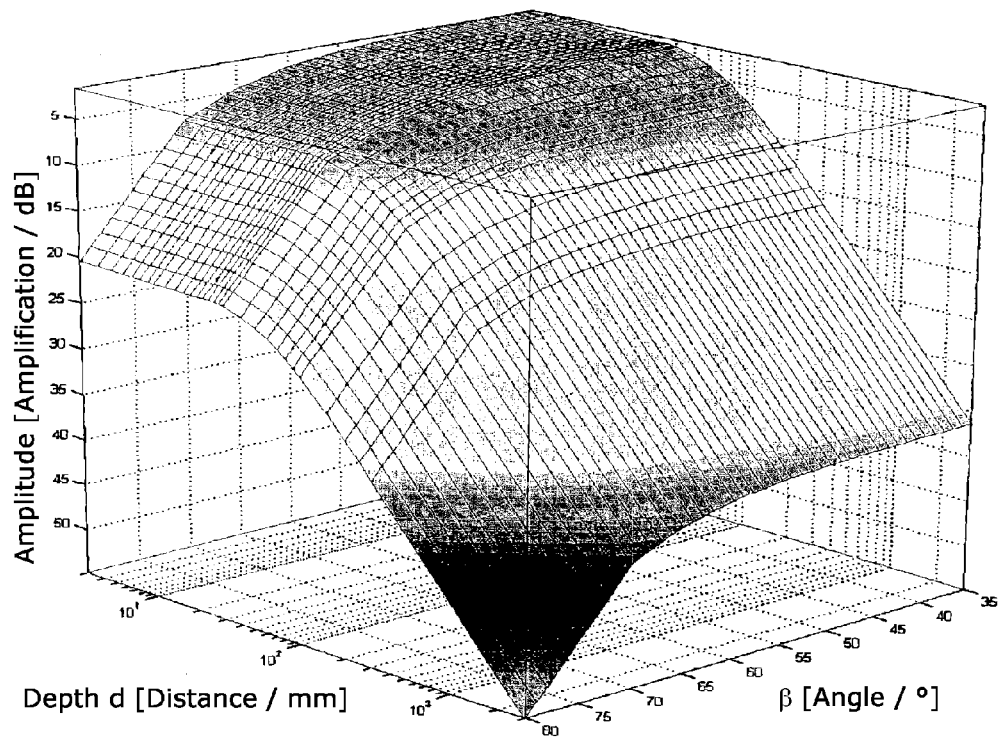

METHOD FOR THE NON-DESTRUCTIVE TESTING OF A TEST OBJECT BY WAY OF ULTRASOUND AND APPARATUS THEREFOR

TECHNICAL FIELD

The subject matter of the present invention is a method for the non-destructive testing of a test specimen by means of ultrasound, wherein, in the scope of the method, an equivalent reflector size for a flaw located in the volume of the test specimen is determined from the ultrasonic echo signals that are recorded within the scope of the method. Furthermore, the subject matter of the present invention is a device that is suitable for carrying out the method according to the invention.

Technical Field

Generic methods are indeed known from the prior art. A flaw in the volume of the test specimen, for example, a void, an inclusion or also a crack, found by means of a pulse echo method based on the insonification of pulsed ultrasound, are characterized by the specification of a value for its equivalent reflector size (ERS). The value of this equivalent reflector size is determined by a comparison of the amplitude of the echo signals that are due to the examined flaw in the volume of the test specimen to a model comparison flaw of a known size. In the so-called reference standard method, the tester compares the echo signals of the examined test specimen to echo signals that he obtains from a reference body equivalent to the test specimen, in which one or more reference reflectors are inserted. For this purpose, for example, cylindrical bores with known dimensions can be inserted into the reference bodies. The echo signals occurring at the bore with an ultrasound reflection are then compared to the echo signals that are obtained with an examination of the test specimen. In the reference standard method, the tester therefore takes measurements with a suitable testing head, which can be, for example, a suitable angle probe, on the test specimen to be examined as well as on the prepared reference body.

In contrast, with the so-called DGS method, the amplitude of the echo signal resulting from a flaw in the volume of the test specimen is compared to a theoretically calculated and/or empirically determined echo signal of a model reference flaw, which is generally assumed to be a flat circular disk and which is located at the same depth in the test specimen as the flaw found during the test carried out on the test specimen. To this end, a so-called DGS diagram is compiled beforehand for the testing head used in the test, which DGS diagram contains the characteristics of the testing head. The curves contained in the DGS diagram indicate the echo amplitude that a reference flaw would produce with a measurement with the testing head used. With a practical inspection task, the tester can then read off the equivalent reflector size of the detected flaw in the volume of the test specimen while making the sound attenuation correction (material-specific sound attenuation) and transfer correction (test specimen-specific coupling losses) for the test specimen directly from the DGS diagram.

In a classic test method according to the DGS method, the tester varies the testing head position and orientation relative to the discovered flaw and attempts to maximize the resulting echo signal hereby. This process is also referred to in materials testing by means of ultrasound as "growing" the ultrasonic signal. The actual determination of the equivalent reflector size of the flaw detected is then carried out for the maximized ultrasonic echo.

Further details on the DGS method are disclosed, for example, in the patent specification U.S. Pat. No. 5,511,425 A, which goes back to the applicant's predecessor in title. Furthermore, the DGS method is described in detail in the book "Werkstoffprüfung mit Ultraschall," (Materials Testing with Ultrasound) J. Krautkrämer and H. Krautkrämer, 5th edition, Springer Verlag, ISBN 3-540-15754-9, Chapter 19.1, pages 343-349. The technical details of the DGS method disclosed here are incorporated by reference into the disclosure of the present application in their entirety.

The disadvantage of the DGS method in its currently widespread form is the fact that for a meaningful characterization of a flaw in the volume of a test specimen an examination with a plurality of testing heads has to be carried out. The reason for this is that for a given flaw a perpendicular insonification into the test specimen does not necessarily produce a maximum echo amplitude. Rather, the insonification angle at which a maximum echo signal can be obtained depends on the orientation of the flaw in the volume of the test specimen. Therefore in order to actually obtain a value for the equivalent reflector size of the flaw detected, which is correlated in a sensible manner with the actual size of the flaw, as a rule different angle probes are used within the scope of the standardized test methods based on the DGS method, which angle probes realize different insonification angles. In practice, this method means a high testing and documentation expenditure for the tester, so that tests are generally carried out only at a few insonification angles. Furthermore, the variation of the insonification angle makes it necessary to change the testing head, which causes additional problems due to the calibration, which is never 100% clear, as well as coupling properties of the testing heads. The interpretation of the ERS values detected on a flaw is also rendered more difficult hereby.

BRIEF SUMMARY

The disclosure provides a method for the non-destructive testing of a test specimen by means of ultrasound, which provides the tester with a new representation of a flaw detected in the volume of the test specimen. Furthermore, a device is to be provided, which is suitable for carrying out the method according to the invention.

The method according to the invention is provided for the non-destructive testing of a test specimen by means of ultrasound. It comprises the following process steps:
  a) Insonification of directed ultrasonic pulses into the test specimen at an insonification angle $\beta$, wherein the insonification angle $\beta$ is adjusted electronically
  b) Recording echo signals that result from the ultrasonic pulses insonified into the test specimen,
  c) Determination of the ERS value of a flaw in the volume of the test specimen from echo signals that can be assigned to the flaw for a plurality of insonification angles $\beta$, and
  d) Generation of a graphic representation of the flaw, from which the dependence of the calculated ERS values of the flaw on the insonification value $\beta$ can be read off at least qualitatively.

It has been found within the scope of complex examinations that the ERS value of a flaw often exhibits a marked dependence on the angle at which the flaw is ensonified. This angle is directly correlated with the insonification angle $\beta$, at which angle the ultrasound insonified into the test specimen according to the method is coupled therein. It has been proven thereby that the observed angular dependence of the ERS value of a flaw allows conclusions to be drawn about essential properties of a flaw, such as, for example, the geometry thereof such as flat or voluminous, in particular the symmetry thereof.

In particular it has been found that a classification of a flaw found in the volume of a test sample can be made based on the angular dependence of its ERS signal. Accordingly, it is much easier for the tester when he has a graphic representation of a flaw that he has detected in the volume of the test specimen, from which graphic representation he can conclude at least qualitatively the dependence of the ERS value of the flaw on the ensonification angle or insonification angle $\beta$.

In an advantageous further development of the method according to the invention, while the method is being carried out, a change of the position of the coupling-in location is detected at which ultrasonic pulses used for the test are insonified into the test specimen. A position detection of this type provides the advantage in particular that the position information can be used to produce a B-scan (X-axis: Position on the surface of the test specimen, Y-axis: depth in the test specimen) or C-scan of the test specimen. Furthermore, the position detection permits a particularly efficient measurement of the angular dependence of the ERS value of a flaw.

In a further preferred embodiment of the method according to the invention, the influence of the electronic adjustment of the insonification angle on the ERS value of the flaw to be determined is automatically compensated in the calculation of the ERS value of the flaw. Corresponding algorithms can be easily integrated into an actuation unit for an ultrasonic testing head.

Preferably, a transmitting test head is used for the insonification of the directed ultrasonic pulses into the test specimen, the ultrasonic transmitter of which transmitting test head comprises a plurality of ultrasonic transducers that can be actuated independently. For the electronic adjustment of the insonification angle $\beta$ the plurality of ultrasonic transducers are then actuated individually exactly in phase such that the angle of emission $\alpha$ of the ultrasonic transmitter is varied. This results directly in a variation of the insonification angle $\beta$ in the test specimen.

It is preferably provided within the scope of the method according to the invention that the influence of the electronic adjustment of the angle of emission angle $\alpha$ and thus the insonification angle $\beta$ on the detected ERS value of the flaw is automatically compensated by calculation in the calculation of the ERS value of the flaw that was detected in the volume of the test specimen from the echo signals that can be assigned to the flaw. The angle of emission and insonification angle $\beta$ are to be considered equivalent within the scope of the present invention, since they are securely linked to one another physically. In particular this means that in the scope of the method according to the invention at least one, but preferably several, of the following corrections is carried out in an automated manner:

Compensation for the change of the virtual ultrasonic transducer size or the aperture associated therewith of the ultrasonic transducer with a changing angle of emission $\alpha$ or insonification angle $\beta$, Compensation for the change of the position of the coupling-in point of the ultrasound emitted by the ultrasonic transducer into the test specimen with changing angle of emission $\alpha$ or insonification angle $\beta$, Compensation for the change of the sound path in the leading body with a changing angle of emission $\alpha$, and Compensation for the change of position of the focus in the test specimen with changing angle of emission $\alpha$ or insonification angle $\beta$, The phased array testing heads already mentioned have particular advantages for the electronic adjustment of the insonification angle $\beta$. However, this does not mean that other ultrasonic testing heads with variable insonification angle could not be used within the scope of the method according to the invention, provided that that the insonification angle is electronically adjustable and also quantifiable.

Within the scope of the method according to the invention, advantageously at least one DGS diagram is used to determine the ERS value of a flaw in the volume of the test specimen from the echo signals reflected by the flaw. This DGS diagram can thereby be specifically for the source of the ultrasonic pulses, that is, in particular specifically for the transmitting test head used. Furthermore, the DGS diagram can be specifically for the material of the test specimen. In a first embodiment, the DGS diagram furthermore exhibits a dependence on the insonification angle $\beta$ of the ultrasound into the test sample or an equivalent angle size. In an alternative approach, the DGS diagram does not show any dependence on the insonification angle $\beta$, instead the influence of the insonification angle $\beta$ on the registered echo amplitude or the ERS value of the flaw is compensated by calculation within the scope of the method.

Furthermore, within the scope of the testing of the test specimen preferably at least one calibration step is carried out. In this step, the amplitude of an echo caused by a reference flaw is detected. The reference flaw is preferably a back wall or a test bore of a test piece, wherein in particular in the case of the back wall echo a separate test piece can also be omitted and the calibration step can be carried out directly on the test specimen itself. Preferably, the calibration step is carried out for a plurality of insonification angles and/or reference flaws, but this is not mandatory.

The device suitable for carrying out the method according to the invention, which will be described in more detail below, thereby preferably offers the possibility of carrying out standardized calibrations steps, in which, e.g., a selection can also be made among a plurality of preset standardized test pieces.

In a preferred embodiment of the method, at least one of the following characteristics of the flaw is shown in the graphic representation generated:

a) The insonification angle $\beta$ at which the ERS value of the flaw is at maximum, b) Information on whether the ERS value of the flaw is essentially constant over different insonification angles $\beta$, or whether it varies at different insonification angles.

In particular in the generated B-scan a detected flaw can be symbolized by a bar, the extension of which along its longitudinal axis correlates with the ERS value of the detected flaw. Advantageously, the same scales are used thereby for the representation of the ERS value and for the X position on the surface of the test specimen. In connection with the present invention, beam means any geometric figure that is mirror-symmetrical with respect to two axes orthogonal to one another, for example, a line, a rectangle, an ellipse, etc. In connection with the present invention, one of the two symmetry axes of the beam is thereby referred to as its longitudinal axis.

In order to increase the interpretability of the B-scan generated within the scope of the method according to the invention, in particular to improve the intuitive comprehensibility of the generated B-scan, it has proven to be advantageous if at least one of the following further characteristics of the detected flaw is shown in the generated B-scan in a suitable manner:

a) The relative amplitude of the flaw echo,
b) The insonification angle β at which the ERS value of the detected flaw is at maximum, e.g., in that the flaw is shown as a bar that is perpendicular to the insonification direction, at which the maximum flaw echo is produced,
c) The relative flaw size,
d) Information on the sound path of the echo, e.g., the leg, from which the flaw echo originates, and
e) Information on whether the ERS value of the detected flaw is identical or different over all of the verified insonification angles β within the range of predetermined flaw limits.

The statement of relative values can relate, e.g., to reference values measured in connection with the testing of the test specimen.

One or more of the following display parameters can be advantageously used in the B-scan for this purpose:
a) The color of the bar,
b) The dimension of the bar transverse to its longitudinal axis (bar width B),
c) The angle of the longitudinal axis of the bar against the surface of the test specimen, and
d) The geometric basic form of the bar.

Several representation options for different flaw characteristics are now explained by way of example in more detail below.

Within the scope of the present invention, relative amplitude of the flaw echo is to be understood as the information on whether the ultrasonic echo originating from the flaw in the volume of the test specimen, i.e. the amplitude of the echo, exceeds a certain predetermined threshold. A threshold of this type can relate, for example, to the measured flaw echo amplitude compared to the amplitude of a reference flaw. In particular, a threshold can be given in "ERS millimeters," e.g., the ERS should be greater than or equal to a registration limit of, for example, 2 millimeters or 5 millimeters.

If within the scope of the method according to the invention the insonification angle β is varied and the insonification angle β determined at which the ERS value of the flaw is at maximum, the tester can be given an indication of the orientation of the flaw in the volume of the test specimen, in that the longitudinal axis of the bar that represents the flaw in the B-scan is shown tilted with respect to the surface of the test specimen. Advantageously, the bar is shown here such that its longitudinal axis stands perpendicular on the acoustic axis of the ultrasound insonified at the angle α for which the ERS value of the flaw is at maximum.

Further information that is relevant for the tester and the documentation is whether the ERS value of the detected flaw is above or below a predetermined registration limit. It is thus possible, for example, to completely suppress flaw signals below a specific threshold in the generated B-scan. Alternatively, flaw signals of this type can also be color-coded or shown as transparent bars in order to show the distance from the registration limit (e.g. in "ERS mm" or dB). In particular the last two representation variants provide the advantage that it can be indicated to the tester that, although a flaw is present in the volume of the test specimen at the tested location, it is so small in terms of its ERS value that it does not need to be documented based on the applicable test specifications.

Furthermore, it can be of interest for the tester to know from which sound path, that is, e.g., "leg" of the insonified ultrasonic beam, the flaw echo results. This information is of interest in particular when a test is being carried out on a test specimen with plane-parallel surfaces, since in this case the situation often occurs that the flaw is not detected by the ultrasonic beam until it has been reflected at least once on the back wall of the test specimen. This information can be determined from the propagation time of the flaw echo and shown in the B-scan, for example, by color-coding the bar graphically for the tester.

Furthermore, the information is of interest to the tester on whether the detected flaw in the volume of the test specimen rather extends in a flat manner or is to be seen as a three-dimensionally extended flaw. The three-dimensionally extended flaws are generally voids or defects that are due to manufacturing and often do not pose a risk of fatigue fractures. In contrast, extended planar flaws are generally correlated with cracks in the test specimen, which can be signs of fatigue and have a marked tendency to spread, which can lead to fatigue fractures. A three-dimensionally extended flaw in the volume of the test specimen is characterized in the scope of the method according to the invention in that the resulting ERS value of the flaw is essentially independent of the insonification angle. In contrast, two-dimensionally extended flaws show a marked dependence on the insonification angle. Here therefore the information on whether it is a planar extended flaw or a three-dimensional flaw can be coded in the bar shown. This can be carried out, for example, by adjustment of the length and width of the bar shown or by the selection of a geometric form that represents the symmetry of the flaw. However, a color-coding can also be used at this point advantageously.

Alternatively to the generation of a B-scan described in detail above, the generation of a C-scan (X-axis: Position in the x direction on the surface of the test specimen, Y-axis: Position in the Y direction on the surface of the test specimen) or the generation of a sector scan (also S-scan, X-axis: distance from the insonification location/depth in the test specimen, Y-axis: Azimuth angle: insonification angle) can be provided and in special cases can be advantageous. All of the above statements on the representation of the determined flaw characteristics in the B-scan can also be applied directly to the furthermore provided C-scans and S-scans.

The method according to the invention makes it possible to now carry out the DGS method provided in many test specifications with modern ultrasonic testing heads that permit an electronic adjustment of the insonification angle in the test specimen, for example, using the phased array technique.

A device according to the invention is provided for the non-destructive testing of a test specimen by means of ultrasound. A device of this type comprises a transmitting test head with an ultrasonic transmitter, which is equipped to insonify directed ultrasonic pulses at an insonification angle β into the test specimen. Furthermore, the device comprises an ultrasonic receiver, which is equipped to record echo signals of the ultrasonic pulses insonified into the test specimen. An actuation and evaluation unit furthermore provided is equipped to actuate the ultrasonic transmitter of the transmitting test head such that the ultrasonic transmitter is triggered to emit ultrasonic pulses. Furthermore, the actuation and evaluation unit is equipped to process the echo signals recorded by the ultrasonic receiver and to determine an ERS value of the flaw from echo signals that can be assigned to a flaw in the volume of the test specimen.

According to the invention the ultrasonic transmitter of the device now has a plurality of ultrasonic transducers that can be actuated independently. Furthermore, the actuation and evaluation unit is equipped to actuate these ultrasonic transducers individually exactly in phase such that the angle of emission α of the ultrasonic transmitter and thus the insonification angle β in the test specimen can be adjusted electronically. Furthermore, the actuation and evaluation unit is equipped to determine the ERS value of a flaw in the volume of the test specimen for a plurality of insonification angles from echo signals that can be assigned to the flaw. Finally, the actuation and evaluation unit is equipped to generate a graphic representation of the flaw mentioned above from which the dependence of the determined ERS value of the flaw on the insonification angle $\beta$ can be read of at least qualitatively.

In particular the generated graphic representation can reflect the ERS value of the flaw in direct dependence on the insonification angle $\beta$. From the angular dependence of the ERS value of the flaw, the tester—as already discussed in detail above—can draw conclusions about essential properties of the flaw. In an alternative approach, the generated graphic representation of the flaw is a B-scan, a C-scan or a sector scan of the test specimen, in which the angle-dependent ERS value of the flaw is recorded in a suitable manner.

In a particularly preferred embodiment of the device according to the invention, which is advantageous in particular in connection with the generation of a B-scan, C-scan or sector scan of the test specimen, the device further comprises a path detection unit, which is equipped to detect a change in the position of the testing head on the surface of the test specimen. A path detection unit of this type can be realized, for example, by means of a mechanical displacement sensor, that is arranged on the testing head itself. However, displacement sensors functioning optically according to the principle of the optical mouse can also be used. Finally, with the use of a phased-array ultrasonic transmitter the changes of the ultrasonic signals, which occur with a position change of the testing head on the surface of the test specimen, can also be utilized for determining a position. Reference has already been made to the corresponding passages in the literature. The use of a linear array renders possible, in addition to the detection of a change in location of the testing head on the surface of the test specimen in the direction of the longitudinal axis of the array, the conduction of an electronic scan in this direction, in that successively different subgroups of transducers are tripped. The use of a two-dimensional phased array permits in particular the detection of a position change in two directions in space, and furthermore the detection of a rotation of the testing head on the surface of the test specimen.

The possibilities of rendering essential flaw properties in the graphic representations of the flaw generated have already been dealt with in detail in connection with the method according to the invention. The device according to the invention is preferably equipped to generate the representations of the flaw explained in connection with the method.

Finally, particular advantages result when the actuation and evaluation unit is equipped to automatically compensate for the influence of the electronic adjustment of the insonification angle $\beta$ on the ERS value of the flaw to be determined in the calculation of the ERS value of the flaw As has already been explained in connection with the method according to the invention, the ERS value of a flaw can be automatically determined, for example, by comparison with a plurality of stored reference values, wherein these reference values can be, for example, one or more DGS diagrams. In this context it is pointed out that for the determination of an ERS value of a detected flaw by means of the method according to the invention for any angle at which the flaw is ensonified, in addition to a DGS diagram, also a reference echo, e.g., from a test specimen must be available.

In a particularly preferred embodiment, a large number of reference values are stored in the actuation and evaluation unit, for example, in the form of DGS diagrams, which are correlated in groups with different insonification angles $\beta$. These reference values can furthermore be testing head-specific thereby. In particular, this can therefore be a testing head-specific quantity of DGS diagrams for various insonification angles $\beta$. Preferably, the testing head is furthermore provided with an electronic identifier that makes it possible for the actuation unit, when the testing head is connected, to recognize independently the testing head type or even the individual testing head and to select the stored testing head (type) specific reference values.

In all of the embodiments, however, the determination of an (insonification angle-specific) ERS value for a detected flaw generally presupposes that a reference value is available, which, e.g., was detected on a test piece at the respective angle or originates from an interpolation between different measured angles.

Particular advantages result when the actuation and evaluation unit is equipped in the calculation of the ERS value of the flaw to automatically compensate for the influence of the electronic adjustment of the insonification angle $\beta$ on the ERS value of the flaw to be determined.

Thus, in a particularly preferred embodiment of the device according to the invention, the actuation and evaluation unit thereof is equipped to automatically convert from the angle of emission $\alpha$ of the ultrasonic transmitter to the insonification angle $\beta$ resulting in the test specimen, in order to automatically compensate for the influence of the electronic adjustment of the insonification angle $\beta$ on the ERS value of the flaw to be determined. In particular, this compensation can be designed in a testing head-specific manner. Furthermore, it will be practically equipped to take into consideration the ultrasound-specific properties of the material of the lead section and of the test specimen such as, for example, the sonic speed.

A further improvement can be achieved when for the automatic compensation for the influence of the electronic adjustment of the insonification angle $\beta$ on the ERS value of the flaw to be determined, the actuation and evaluation unit of the device according to the invention is equipped to automatically compensate for the variation of the virtual ultrasonic transmitter size associated with the electronic variation of the insonification angle $\beta$ and thus the aperture of the testing head. The virtual ultrasonic transmitter size results from a projection of the actual geometric dimension of the ultrasonic transmitter onto one perpendicular to the electronically adjusted emission direction of the ultrasonic transmitter. If the ultrasonic transmitter emits at an angle of emission $\alpha$ differing from 0°, this results directly in a reduction of the virtual ultrasonic transmitter size. Since the ultrasonic transmitter size may be included in the calculation of the ERS value of a detected flaw, as the case may be, a corresponding automatic compensation must take place here.

A further improvement results when the actuation and evaluation unit is equipped to automatically compensate for the influence of the displacement of the coupling-in location $X_0$, which is associated with an adjustment of the angle of emission $\alpha$ or of the insonification angle $\beta$, on the ERS value of the flaw to be determined.

Finally, an automatic compensation can also be provided for the position change of the focus in the test specimen, which results during a variation of the angle of emission $\alpha$ due to the change of the sound path length in the leading body resulting therefrom.

In conclusion, it should be pointed out that the automatic compensation according to the invention for the influence of the electronic adjustment of the insonification angle $\beta$ on the ERS of the flaw to be determined on the basis of stored DGS diagrams can be carried out in two different ways. On the one hand, the actuation and evaluation unit can be equipped to standardize the actual measured values (i.e., time-resolved echo signals) taking into account the influence of the adjustment of the insonification angle β, i.e., for example, to convert to the results of a conventional testing head with fixed insonification angle β. These are then compared to a standardized DGS diagram.

On the other hand, the testing head-specific influences of the electronic angle adjustment on the echo signals can already be taken into account with the production of the DGS diagrams stored in the actuation and evaluation unit, i.e., the compensation to be carried out is already taken into account in the stored DGS diagrams. This implementation is also covered by the method according to the invention and the device according to the invention.

BRIEF DESCRIPTION OF THE DRAWINGS

Further advantages and features of the device according to the invention and the method according to the invention are shown by the subordinate claims and the exemplary embodiments, which are explained in more detail below based on the drawing.

They show:

FIG. 3: A representation of the maximum echo amplitude Amax as a function of the insonification angle β, FIG. 4: An angle-resolved testing head-specific DGS diagram.

DETAILED DESCRIPTION

Figure 1:
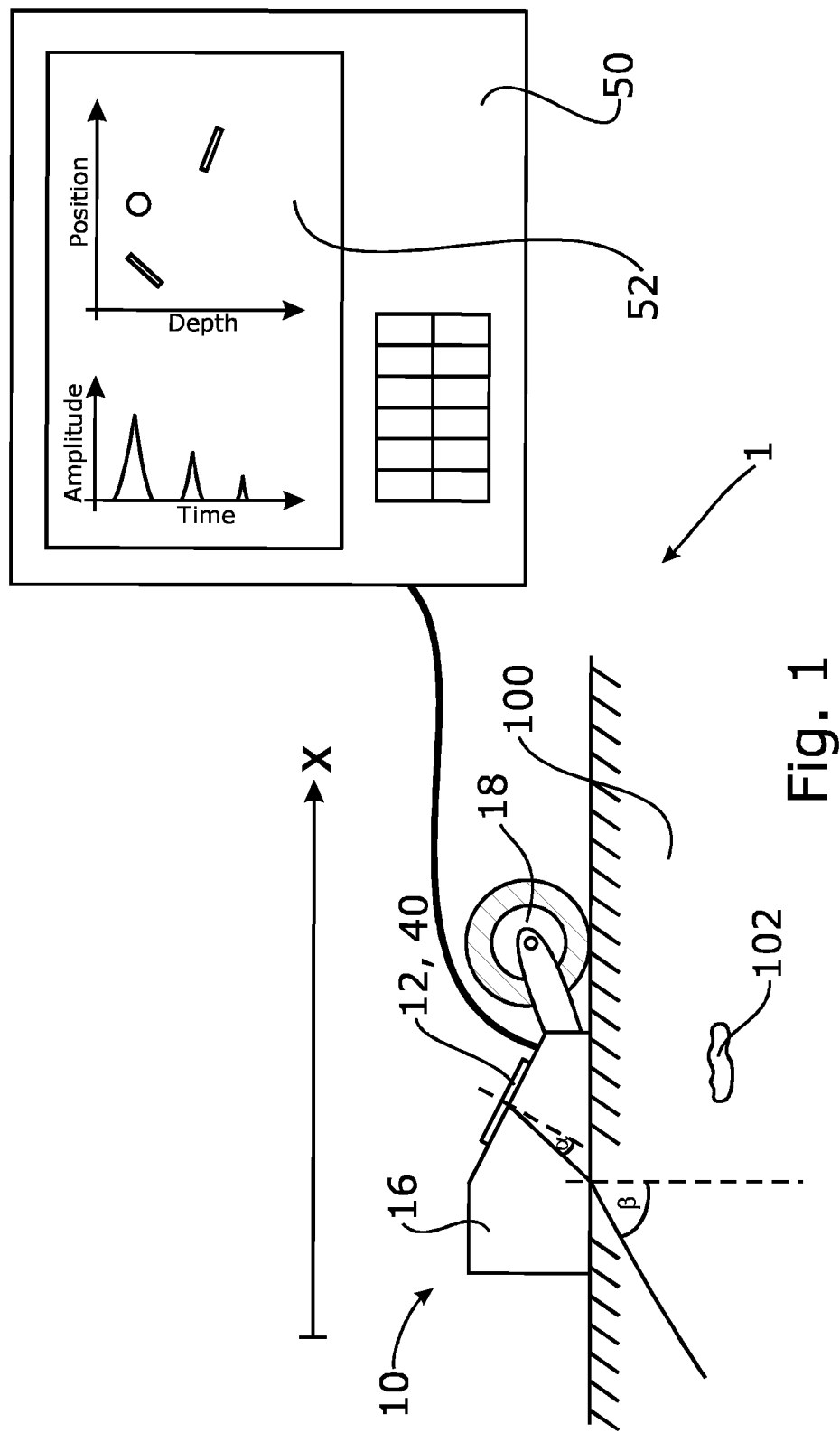
FIG. 1: A diagrammatic representation of a device according to the invention for the non-destructive testing of a test specimen.

FIG. 1 shows an exemplary embodiment of a device 1 according to the invention for the non-destructive testing of a test specimen 100 by means of ultrasound. The device 1 comprises a transmitting test head 10, which for its part comprises a lead section 16 and an ultrasonic transmitter 12 arranged thereon. The ultrasonic transmitter 12 is thereby arranged on the lead section 16 such that with a triggering of the ultrasonic transmitter 12 to emit ultrasonic pulses, these are essentially coupled into the lead section 16. The lead section 16 can thereby be formed, for example, by a body of Plexiglass®, as is known in principle from the prior art. Preferably, the elements of the transmitting test head 10 are combined in a single housing, which is not shown in the figure for reasons of clarity. The transmitting test head 10 shown is an angle probe, which is provided to couple into the test specimen 100, the ultrasonic pulses emitted by the ultrasonic transmitter 12 at an angle of incidence β, which is measured against the face normal of the incident face of the test specimen 100. The use of angle probes is optional and not mandatory, depending on the case, testing heads for a perpendicular insonification (i.e., β=0°) can also be used.

The ultrasonic transmitter 12 used in the transmitting test head 10 is an ultrasonic transmitter of the phased array type, i.e., the ultrasonic transmitter 12 comprises a plurality of ultrasonic transducers 14, which form at least one linear arrangement and can be actuated individually. The longitudinal axis of the at least one linear array of the ultrasonic transducers 14 is thereby oriented in the direction labeled by X. By means of targeted adjustment of the phase position between the individual ultrasonic transducers 14, it is possible to dynamically influence the angle of emission a, i.e. the beam direction, within wide limits.

In the exemplary embodiment shown the transmitting test head 10 comprises a mechanical displacement sensor 18, which mechanically scans the movement of the transmitting test head 10 on the surface of the test specimen 100 and provides corresponding position information, e.g., to an actuation unit 50 connected to the transmitting test head 10. Alternatively, the displacement sensor 18 can also operate in a contactless manner, e.g., according to the principle of the optical mouse. The displacement sensor 18 is—regardless of the type—preferably able to detect the movement of the transmitting test head 10 in two directions independent of one another on the surface of the test specimen 100. Particular advantages result when rotary movements of the transmitting test head 10 on the surface of the test specimen can also be detected. Based on the technology that is disclosed in the patent specification U.S. Pat. No. 7,324,910 B2, as well as the further development thereof which is disclosed in German patent application 10 2007 028 876.1 dated Jun. 26, 2007, a separately designed displacement sensor can be omitted completely, since the entire position information can be obtained from the signals of the ultrasonic 12 itself.

Connected to the transmitting test head 10 is an actuation unit 50, which is equipped to actuate the ultrasonic transducers 14 arranged in the ultrasonic transmitter 12 of the transmitting test head 10 individually exactly in phase. Furthermore, the actuation unit 50 is equipped to be connected to an ultrasonic receiver 40 in order to receive echo signals reflected back from a test specimen 10, which echo signals result from the ultrasonic pulses insonified from the ultrasonic transmitter 12. In the exemplary embodiment shown here, the ultrasonic trans-mitter 12 arranged in the transmitting test head 10 also serves as an ultrasonic receiver 40. To this end, the ultrasonic transducers 14 contained in the ultrasonic transmitter 12 embodied separately and actuatable separately, are electrically interconnected after the emission of a transmitted pulse to form a large-area ultrasonic transmitter 12, which then acts as the ultrasonic receiver 40. However, of course it is also possible to use a separately embodied ultrasonic receiver 40, which can be arranged, e.g., in a separately embodied receiving test head. A separate receiving test head of this type would likewise comprise a lead section in the present exemplary embodiment, according to the lead section 16 of the transmitting test head 10.

For the non-destructive testing of a test specimen 100 for, for example, flaws 102 concealed in the volume of the test specimen 100, the transmitting test head 10 is connected to the control unit 50 and placed on the surface of the test specimen 100. The acoustic coupling of the transmitting test head 10 to the test specimen 100 is carried out as a rule using a suitable coupling means, which can be, for example, water, oil or also a water-based gel.

The test specimen 100 is preferably a mechanical workpiece or tool; however, it can also be a biological sample.

Now the tester moves the transmitting test head 10 back and forth 10 along the direction labeled by X in FIG. 1 on the surface of the test specimen 100. At the same time he observes the display on a display device 52 assigned to the actuation unit 50, which display device in the exemplary embodiment shown is integrated as a display into the actuation unit 50. An A-image is shown on the display device 52 in the exemplary embodiment shown, in which the amplitude of the ultrasonic pulses reflected back is shown for the given insonification location X as a function of the time. If the sound ray emitted by the transmitting test head 10 strikes a flaw 102 in the volume of the test specimen 100, i.e., an ultrasound-reflecting structure such as a defect, a void or a crack, part of the insonified sound ray is reflected back and reaches on the same route back to the ultrasonic transmitter 12 of the transmitting test head. As mentioned, this also acts at the same time as the ultrasonic receiver 40, which converts the sound signal reflected back into an electric signal, which is then delivered, optionally amplified in a suitable manner, to the actuation unit 50. In the actuation unit 50 the echo signal received, which is generally present as an electrical signal, but which can also, if necessary, be transmitted by the transmitting test head 10 in the form of an optical signal, is processed in a suitable manner, this can be carried out, for example, by highly time-resolved AD-conversion and signal processing. Subsequently, the signal is shown in the form of the A-scan described above on the display device 52. If the insonified ultrasonic beam meets a flaw 102, this results in echo signals that are directly visible in the A-scan. The approach described above is thereby advantageously carried out with a fixed insonification angle $\beta$.

Figure 2A:
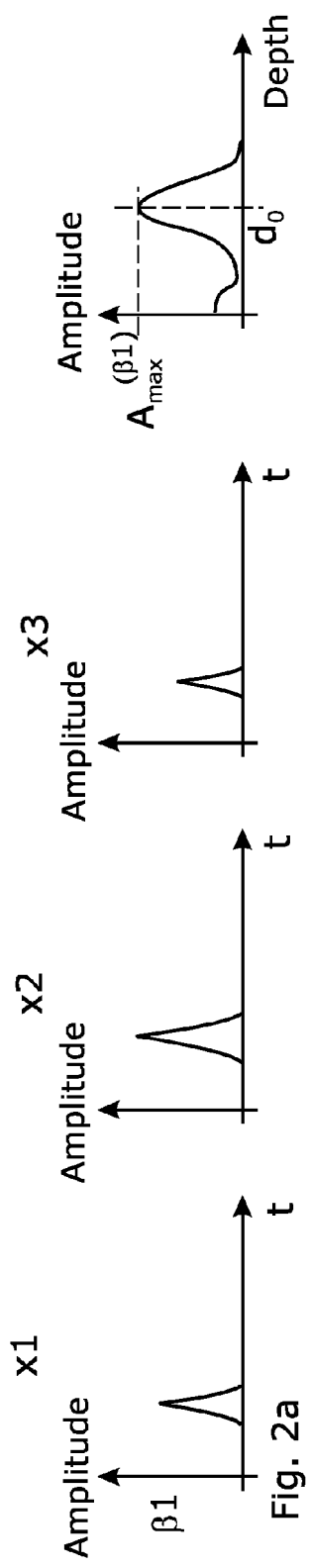
FIG. 2a-2c: An A-scan of the test specimen, recorded at different insonification positions x as well as at different insonification angles β, as well as the progression of the maximum amplitude Amax for a given insonification angle β as a function of the depth d in the test specimen.

When the tester has discovered a flaw 102 with the mode of operation described above, he tries by variation of the X-position of the transmitting test head 10 on the surface of the test specimen 100, to maximize the amplitude of the resulting flaw signal, i.e., to grow the signal. This growing of the signal is also carried out for a fixed insonification angle $\beta 1$. The A-scans resulting with the growing of the echo signal at various insonification locations X1, X2 and X3 are shown in FIG. 2a. It is clear that due to the change of the propagation path in the test specimen 100 the echo signal occurs at different times, but also varies in its maximum amplitude. This is because in the displacement of the transmitting test head 10 on the surface of the test specimen 100, the center of the sonic cone in which the highest sonic pressure prevails, is pushed over the flaw 102. As a rule, the maximum amplitude in the echo signal results when the sound ray strikes the flaw 102 centrally. If the envelope curve of all echo signals is determined for a fixed insonification angle $\beta 1$ with a variation of the insonification location X, a representation of the echo amplitude is obtained as a function of the propagation time or the depth of the flaw 102 in the test specimen 100, as is illustrated in the right-hand diagram of FIG. 2a. From this diagram the maximum echo amplitude Amax ($\beta 1$) can be determined, which results for the selected insonification angle $\beta 1$.

Figure 2B:
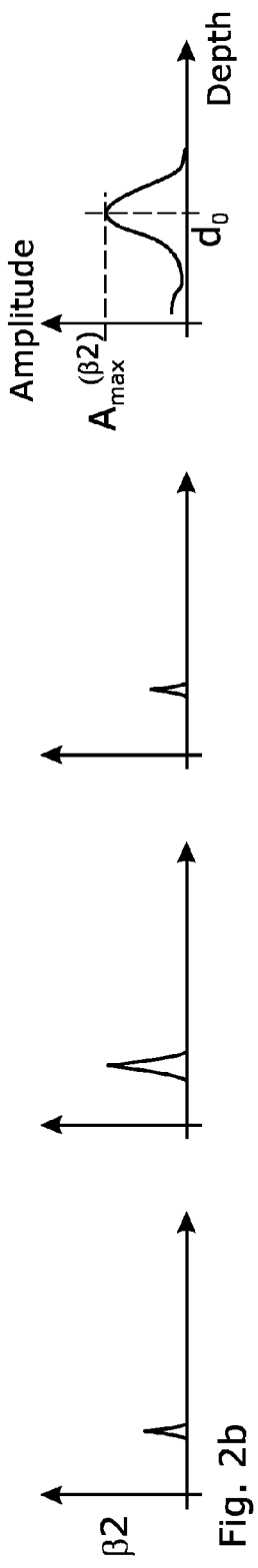

Thereafter the tester can vary the insonification angle $\beta$, so that he carries out the same investigation for a changed insonification angle $\beta 2$ once again. Alternatively, an automatic change of angle is also possible within the scope of a partially automated test method. This also results in a diagram for the progression of the amplitude as a function of the time or of the depth of the flaw 102 in the test specimen 100. A diagram of this type is shown on the right in FIG. 2b. The maximum echo amplitude resulting here with the insonification angle $\beta 2$ does not necessarily have to correspond to the echo amplitude with the first selected insonification angle $\beta 1$, as a rule there will even be a deviation here, unless it is a regularly shaped flaw.

If the different propagation times that result through the different insonification angles $\beta 1$ and $\beta 2$ are compensated for, in the referenced representation of the envelope curve Amax ($\beta$) the peaks lie essentially at the same point D0. However, if a propagation time compensation of this type is omitted, the peaks come to rest at different points.

Figure 2C:
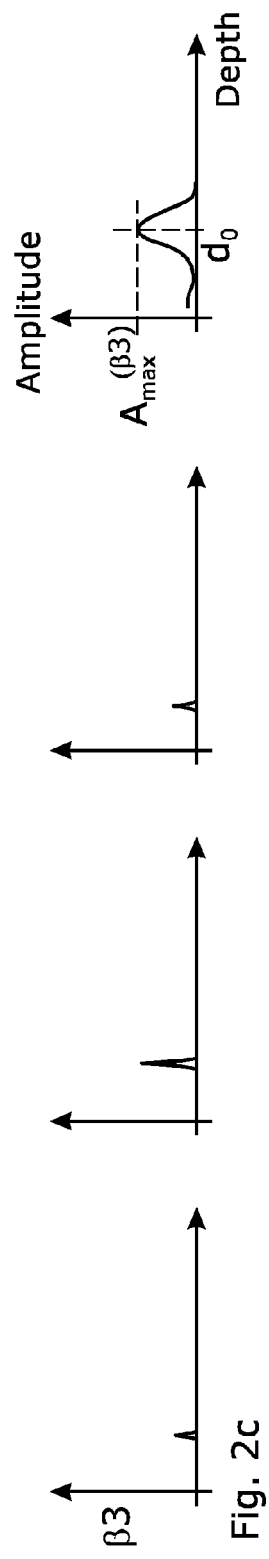

In FIG. 2c the result of the same method for an insonification angle $\beta 3$ changed again is shown by way of example.

The insonification angle $\beta$ is electronically tuned with the approach described above utilizing the advantageous transmission properties of an ultrasonic trans-mitter 12 of the phased array type.

In an alternative embodiment, the actuation unit 50 is equipped to automatically optimize a possibly resulting echo signal for a given insonification location X by variation of the insonification angle $\beta$.

If the maximum amplitudes Amax resulting for different insonification angles $\beta$ are plotted over the corresponding insonification angle $\beta$, a diagram is obtained such as can be seen from FIG. 3. Now that insonification angle $\beta$ for which the examined flaw 102 shows the maximum echo amplitude Amax, can be determined from this diagram or the echo data on which it is based. The angular dependence of the ultrasonic reflection of the flaw 102 can also be illustrated and analyzed from this in a simple manner. Possible interpretations of the behavior achieved with regard to the type of flaw 102 have already been described above.

In the preparation for the practical testing of the test specimen explained above —as is known from the prior art for testing heads with fixed insonification angle $\beta$—so-called DGS diagrams are determined. A DGS diagram thereby shows the echo amplitude of circular disk reflectors of different diameters and also of an extended flat reflector (back wall echo) as a function of the distance, i.e. as a function of the depth d in the test specimen. In contrast to the DGS diagrams and devices for ultrasonic measurement previously known from the prior art, in which testing head-specific DGS diagrams are stored, for example, in digital form, within the scope of the present invention the DGS diagrams are additionally recorded or generated in an angle-resolved manner and optionally stored in the actuation unit 50. FIG. 4 shows by way of example a DGS diagram of this type for a predetermined diameter of a circular disk reflector as a function of the distance d and as a function of the angle $\beta$.

To determine the ERS value of a flaw with the aid of a phased array testing head, which permits an electronic variation of the insonification angle $\beta$ into the test specimen 100, an adjustment of the general DGS diagram known from the prior art (cf. U.S. Pat. No. 5,511,425 A), which is based on theoretical considerations, can be necessary for various reasons. On the one hand, a calibration of the generally testing head-specific DGS diagram is necessary in order to take into account the ultrasonic properties of the material of the test specimen and to compensate for testing head-specific effects such as the aging of the ultrasonic transducer or a changed coupling of the transmitting test head to the test specimen. To this end, before an actual test of a test specimen 100 is carried out, in most test specifications conducting a calibration step is required in order to calibrate the general DGS diagram, which can be already stored in the device 1.

Furthermore, it must be taken into account with an electronic variation of the insonification angle $\beta$ with the aid of a phased array testing head that the ultrasonic properties of the testing head change directly through the change of angle itself. For this reason, the general DGS diagram, which was determined for a specific insonification angle, must be converted for other (electronically adjusted) insonification angles β. In particular, it is possible to carry out this conversion in the device itself, so that a storage of a plurality of testing head-specific DGS diagrams for different insonification angles β is not necessary. In an alternative approach, of course, it is also possible to store a plurality of, e.g., testing head-specific ones in the device 1, which relate to a plurality of insonification angles β. Here too the DGS diagrams can be determined empirically or calculated theoretically.

Figure 5:
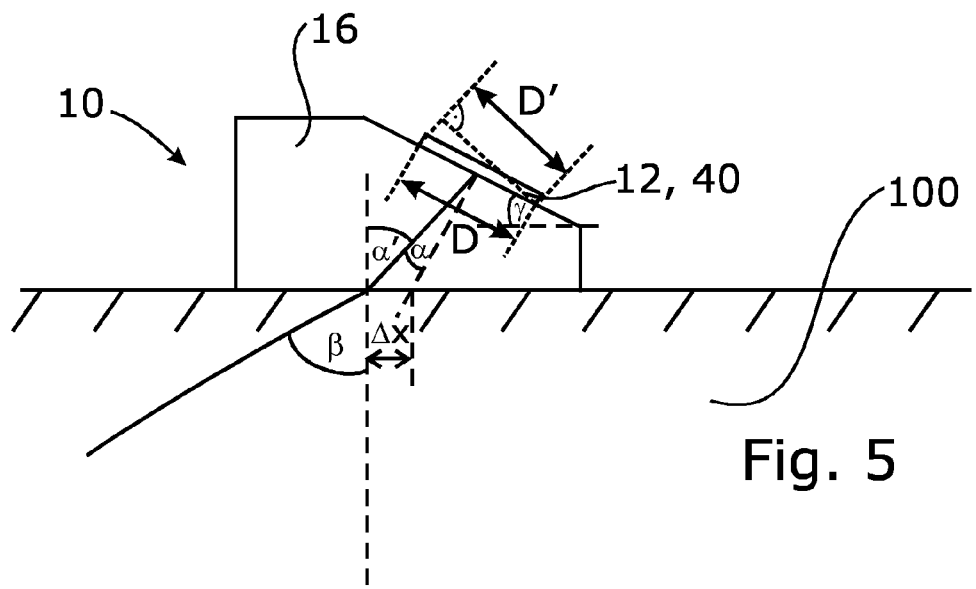
FIG. 5: A diagrammatic representation of the beam geometry at the testing head.

As has already been explained above, the insonification angle β can be electronically tuned with the use of a device according to the invention. As can be seen from FIG. 5, for example, with an angle probe with a lead section, in an electronic tuning of the insonification angle β, the coupling-in point of the sound ray in the test specimen changes by ΔX and the diameter of the sound ray changes with its transfer from the lead section into the test specimen. This can also be interpreted as a virtual change of the dimensions of the ultrasonic transmitter 12 (D->D'), which likewise has to be taken into consideration in the recording of the DGS diagrams mentioned above. By means of simple geometric deliberations and the law of acoustic refraction, it is possible to easily calculate the influence of the electronic change of the insonification angle β on the change of the coupling-in point and the size of the virtual ultrasonic transmitter (12).

In order now to determine an equivalent reflector size ERS for the flaw detected in the volume of the test specimen, the tester—as with the devices already known from the prior art with testing heads with fixed insonification angle β—has that DGS curve represented on the display device 52 of the actuation unit 50 that corresponds to the electronically adjusted insonification angle β at which the maximum echo signal Amax resulted. The DGS curve was thereby calibrated prior to the actual measurement on reference flaws, which can be inserted in test specimens, for example. The "calibration" is a calibration of the sensitivity of the testing head used. As a rule, the reference echo needed for this purpose is obtained from back wall echoes on the standardized so-called "K1" or "K2" test pieces (depending on the frequency of the testing head used). Since in these cases, these are not flat back walls, a circular arc correction (generally given by the manufacturer of the testing head) must also be carried out. Reference reflectors from the component, however, are rather rare.

The DGS curve displayed on the screen corresponds to a predetermined equivalent reflector size, which generally corresponds to the registration limit specified by the test specification. If a flaw is found, the echo of which exceeds the DGS curve shown on the screen, e.g., the resulting equivalent reflector size ERS is given automatically by the actuation unit 50 (either in dB over the registration limit or directly in millimeters). In the DGS curve, while plotting the propagation time of the pulse up to the detected flaw, the tester can therefore read off directly the equivalent reflector size ERS of the flaw.

In a largely automated test routine, the tester scans the surface of the test specimen 100 in the manner described above until he detects echo signals which in his opinion originate from a flaw 102 in the volume of the test specimen 100. If necessary, he performs a certain optimization of the flaw signal manually here before he shifts the actuation and evaluation unit 50 of the device 1 according to the invention to an automatic measurement mode. In this the actuation unit 50 actuates the ultrasonic transmitter 12 such that the coupling-in point of the sound ray in the test specimen is displaced in the X direction on the surface of the test specimen 100. At the same time, the actuation unit 50 records the amplitude of the resulting flaw echo as a function of the coupling-in point and determines the maximum echo amplitude. The insonification angle β is kept constant thereby.

In a subsequent process step, the actuation unit 50 varies the insonification angle so that the flaw 102 to be measured in the volume of the test specimen 100 is insonified at a different angle β2. Here too the actuation unit 50 varies the coupling-in point of the emitted sound ray into the test specimen through suitable actuation of the ultrasonic transmitter 12, wherein at the same time the resulting echo amplitude is recorded. Here too the maximum echo amplitude Amax (β2) at the adjusted insonification angle β2 is determined, i.e., the tester "grows" the echo signal.

By comparison with one or more testing head-specific and angle-specific DGS diagrams, the actuation unit 50 of the device according to the invention then automatically determines the ERS value of the measured flaw 102. To this end the actuation unit 50 automatically compensates for the influence of the electronic variation of the angle of emission a of the ultrasonic transmitter 12 on the coupling-in point of the ultrasonic beam into the test specimen and thus on the propagation time of the ultrasonic pulses from the ultrasonic transmitter 12 up to the flaw 102. Furthermore, the actuation unit 50 likewise automatically compensates for the influence of the electronic variation of the angle of emission a of the ultrasonic transmitter 12 on the virtual transmitter size, as has been described above. The actuation unit 50 also automatically compensates for the change of position of the focus in the test specimen through the changed sound path in the leading body. Finally, the actuation unit 50 automatically converts from the angle of emission a to the insonification angle β, wherein optionally the material properties of the test specimen are taken into consideration.

As a result, an ERS value of the flaw 102 detected in the volume of the test specimen 100 as well as the insonification angle β at which the maximum flaw signal Amax results are obtained from the test method carried out manually as well as from the test method carried out automatically. These data can then be recorded.

Figure 6:
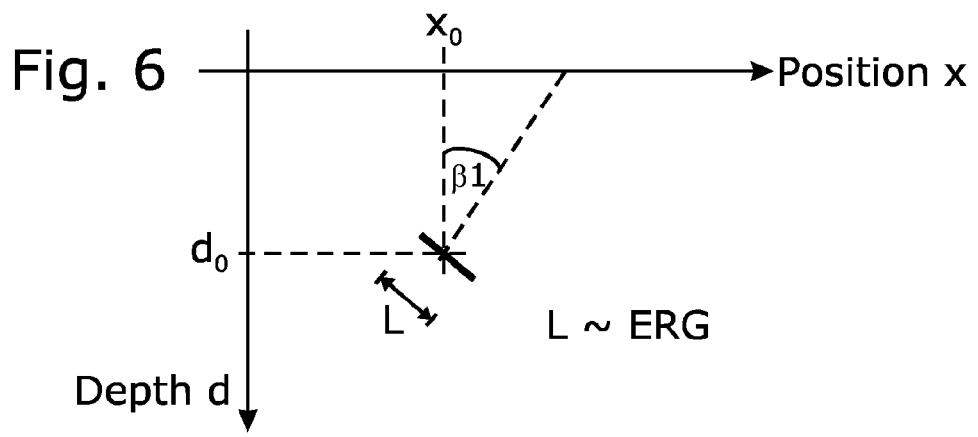
FIG. 6: An image representing a B-Scan of the specimen, in which a flaw is represented by an associated ERS value.

If additional position information on the testing head is available, the test result can be illustrated furthermore in a B-scan, as is shown by way of example in FIG. 6, or also in a C-scan or S-scan. Thus a bar of the length L shown in the B-scan, the X-position of which on the surface of the test specimen corresponds to that position X0 at which the flaw is located by calculation. In the Y direction the bar is arranged at the depth $D_0$, which corresponds to the calculated depth of the flaw in the volume of the test specimen 100. Furthermore, the length L of the bar that represents the measured flaw 102 is directly linked to the equivalent reflector size ERS of the flaw determined in the scope of the test method according to the invention. Advantageously, the orientation of the bar is furthermore directly correlated with that insonification angle β at which the maximum echo signal Amax results. To this end, the longitudinal axis of the bar can be shown tilted with respect to the X-axis such that the bar is oriented perpendicular to the sound propagation direction that corresponds to that insonification angle β at which the maximum echo signal results. The orientation of the bar in the B-scan shown in FIG. 6 provides the tester directly with information on the orientation of the measured flaw in the test specimen, which likewise can be recorded and stored. The B-scan shown diagrammatically in FIG. 6 is thereby preferably likewise shown to the tester on the display device 52, which is connected to the actuation device 50. Preferably, the actuation device 50 is equipped to transmit the stored data to a PC where they can be subjected to a further evaluation.

Figure 7:
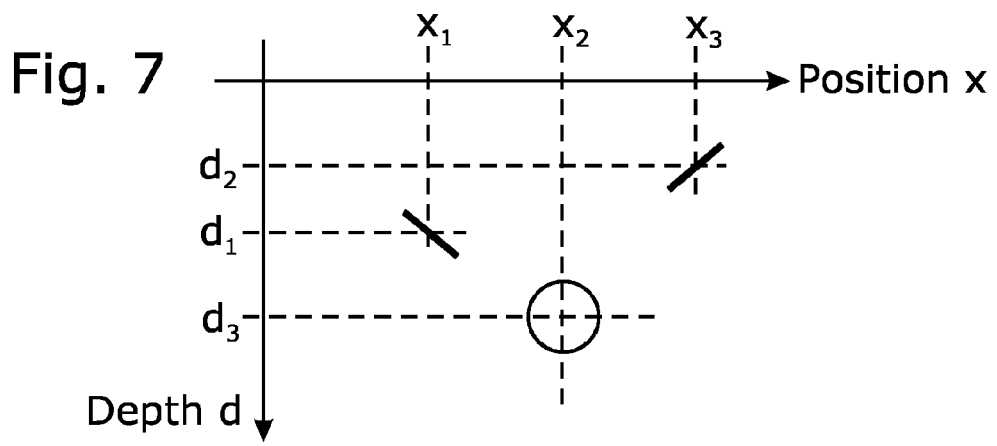
FIG. 7: A representation according to FIG. 6 of the test specimen with a plurality of flaws that have different reflection properties.

FIG. 7 finally shows a B-scan of a test specimen 100, from which three flaws 102 in the volume of the test specimen 100 can be seen. The flaws thereby lie at positions X1, X2 and X3. The flaws 102 detected at positions X1 and X3 thereby show a marked dependence of the echo signals on the insonification angle, i.e., the variation of the maximum flaw echo amplitude Amax resulting with a change of the insonification angle β exceeds a specific threshold value. It can be concluded from this that this is a planar extended flaw 102; accordingly, these flaws are shown in the B-scan of FIG. 7 as essentially one-dimensional symbols.

The flaw 102 detected at position X2, however, shows an echo amplitude essentially independent of the insonification angle β, i.e., the resulting variation of the echo amplitude remains below a predetermined threshold. A rather uniform three-dimensional extension of the flaw 102 can be concluded from this, which is shown in the B-scan of FIG. 7 by a two-dimensional flaw symbol (e.g., a circular disk as shown), the diameter of which is correlated with the equivalent reflector size ERS of this flaw.

Figure 8:
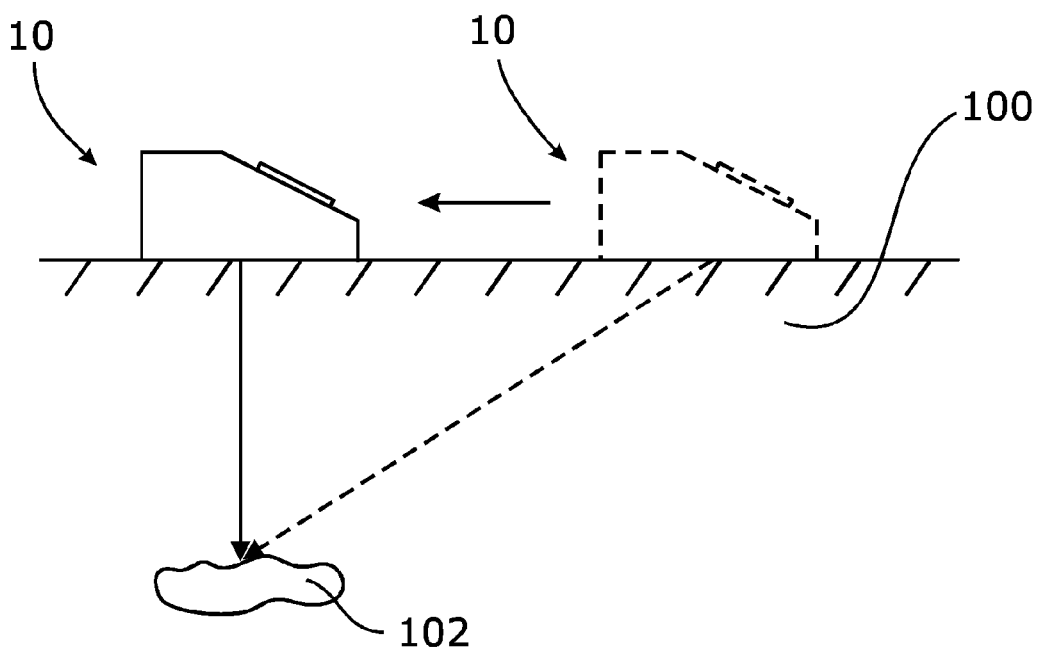
FIG. 8: A diagrammatic representation of a method for detecting the angular dependence of the ERS value of a flaw in the volume of the test sample.

On the basis of FIG. 8 a new method is now illustrated, which likewise is implemented in the device 1 according to the invention. In a first process step, the transmitting test head 10 is actuated by the device 1 such that it insonifies ultrasonic pulses at a fixed angle of incidence β into the test specimen 100. When the tester has found a flaw 102 in the volume of the test specimen 100, he grows the flaw signal until the signal amplitude is at maximum. In a next step, he activates a "scan" function, in which the testing head 10 is actuated by the device 1 such that the insonification angle β in the test specimen 100 is electronically varied within a predetermined interval. The device 100 is furthermore equipped to then determine from the flaw echoes received at the different insonification angles β the maximum flaw echo and the associated insonification angle β Max. If the position of the transmitting test head 10 is changed on the surface of the test specimen 100, a changed insonification angle β results, at which the flaw echo is maximal, since a maximum flaw echo is generally obtained when the flaw is detected centrally by the ultrasonic beam. If, as described above, an electronic angle-scan is carried out, the device 1 can detect fully automatically that changed insonification angle β for which the flaw echo is at maximum. Via a variation of the position of the transmitting test head 10 on the surface of the test specimen 100, the maximum flaw echo for different insonification angles β can be determined automatically by means of the method described above. The position of the transmitting test head 10 on the surface of the test specimen 100 can thereby on the one hand take place through a mechanical movement of the transmitting test head 10, but it can also be varied virtually by carrying out a linear scan within the plurality of individual ultrasonic transducers 14 in the ultrasonic transmitter 12 (so-called "electronic linear scan").

If at least one DGS diagram, e.g., according to FIG. 4, is stored in the device, which, for example, can have been theoretically calculated or determined by means of practical measurements, then from the maximum flaw echo amplitude determined for a certain insonification angle β, the ERS value of the flaw for this angle detected can be determined from the diagram. As the case may be, it can be necessary to calibrate the DGS diagram/s stored in the device in a testing head-specific or material-specific manner based on a reference echo obtained on a test piece, which reference echo optionally is recorded at different insonification angles, before the actual testing of the test specimen 100 is carried out. The DGS method thus permits in particular the automatic compensation for the sound paths resulting for the different insonification angles in the test specimen.

Alternatively, in the determination of the angular-dependent ERS-value of a flaw 102 in the volume of the test specimen 100, the device 1 can also utilize the position information that is supplied by the path detection unit 18. As described above, in a first step for a fixed insonification angle β the position of the transmitting test head 10 on the surface of the test specimen 100 is sought for which the amplitude of the flaw echo is at maximum. Subsequently a "trace" function on the device 1 is activated by the tester. When this is activated, the device 1 is equipped with a changing position of the transmitting test head 10 by means of suitable geometric calculations to adjust that insonification angle β on the transmitting test head 10 at which the flaw 102 in the test specimen is centrally detected by the ultrasonic beam even with the changed transmitting test head position. In the case of a displacement of the transmitting test head 10 on the surface of the test specimen 100, the detected flaw 102 is then recorded with the aid of the trace function mentioned at any time centrally by the ultrasonic beam, so that the resulting flaw echo can be seen as the maximum flaw echo for the set insonification angle β. The maximum flaw echo can thus be recorded as a function of the insonification angle β directly by variation of the position of the transmitting test head 10 on the surface of the test specimen 100 and from this the angle-dependent ERS value of the flaw 102 can be determined as a function of the angle β.

Figure 9A:
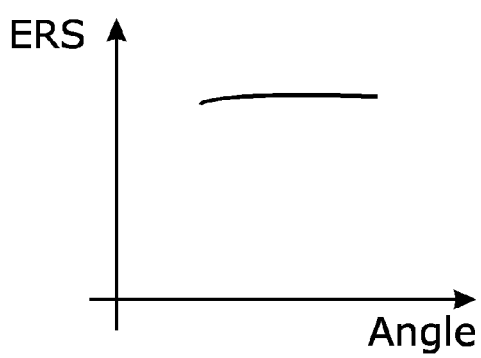
FIGS. 9a, 9b: Diagrammatic representations des angle-dependent ERS value of two different flaws in the volume of the test specimen.
Figure 9B:
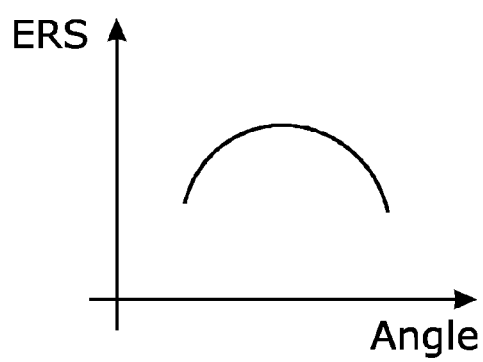

FIGS. 9a and 9b finally show by way of example the angle-dependent progression of the ERS value of two different flaws 102 in the volume of the test specimen 100. FIG. 9a thereby shows a flaw 102, the ERS value of which varies only weakly with the insonification angle β. This is therefore evidently a flaw 102, the ultrasonic reflection of which practically does not depend on the angle at which the flaw is struck by the ultrasonic beam. Consequently, it is to be assumed that the flaw is largely isotropic, at least with respect to that direction in space in which the position of the transmitting test head 10 was varied during the above-referenced examination.

FIG. 9b, however, shows a flaw, the ERS value of which depends very greatly on the insonification angle β. That means the ultrasonic reflection of the flaw 102 depends greatly on the angle at which the flaw 102 is detected by the ultrasonic beam. At least with respect to the direction in space in which the transmitting test head is moved to detect the angular dependence of the ERS value, the flaw 102 to be classified is to be seen as very anisotropic. It can also be a crack, for example, which in all probability must be registered and therefore should be graphically emphasized in a suitable manner, for example, in a B-scan, C-scan or sector scan generated by the device 1, as has already been explained above.

The invention claimed is:
1. Method for the non-destructive testing of a test specimen by means of ultrasound, comprising the following process steps:
   a. Insonification of directed ultrasonic pulses into the test specimen at an insonification angle β, wherein the insonification angle β is adjusted electronically,
   b. Recording echo signals that result from the ultrasonic pulses insonified into the test specimen,
   c. Determination of the ERS value of a flaw in the volume of the test specimen from echo signals that can be assigned to the flaw for a plurality of insonification angles β, and d. Generation of a B-scan, a C-scan or a sector scan as a graphic representation of the flaw, wherein this contains an at least qualitative representation of the dependence of the calculated ERS values of the flaw on the insonification angle β.

2. Method according to claim 1, wherein a change of the position of the coupling-in location is detected at which the ultrasonic pulses are insonified into the test specimen.

3. Method according to claim 1, wherein the influence of the electronic adjustment of the insonification angle β on the ERS value of the flaw to be determined is automatically compensated in the calculation of the ERS value of the flaw.

4. Method according to claim 1, wherein
   a. For the insonification of directed ultrasonic pulses a transmitting test head is used, the ultrasonic transmitter of which comprises a plurality of ultrasonic transducers that can be actuated independently, and
   b. For the electronic adjustment of the insonification angle β the plurality of ultrasonic transducers are actuated individually exactly in phase such that the angle of emission α of the ultrasonic transmitter is varied.

5. Method according to claim 1, wherein at least one DGS diagram is used to determine the ERS value of the flaw from the echo signals.

6. Method according to claim 5, wherein the DGS diagram is specifically for the source of the ultrasonic pulses.

7. Method according to claim 5, wherein the DGS diagram has a dependence on the insonification angle β.

8. Method according to claim 5, wherein the DGS diagram is independent of the insonification angle β and the influence of the insonification angle β on the registered echo amplitude is compensated by calculation.

9. Method according to claim 1, wherein within the scope of the testing of the test specimen a calibration step is carried out at least once, in which the amplitude of an echo caused by a reference flaw is detected.

10. Method according to claim 9, wherein the reference flaw is a back wall or a test bore of a test piece.

11. Method according to claim 9, wherein the calibration step is carried out for a plurality of insonification angles β.

12. Method according to claim 1, wherein at least one of the following characteristics of the flaw is shown in the graphic representation of the flaw produced:
   a. Insonification angle β, at which the ERS value of the flaw is at maximum,
   b. Information on whether the ERS value of the flaw is essentially constant over different insonification angles β.

13. Method according to claim 12, wherein
   a. The flaw is shown as a bar in the representation produced, and
   b. At least one of the following display parameters is used for coding the flaw characteristics to be represented:
      i. Color,
      ii. Angle of the longitudinal axis of the bar against the surface of the test specimen,
      iii. Geometric basic form of the bar.

14. Device for the non-destructive testing of a test specimen by means of ultrasound, with
   a. A transmitting test head with an ultrasonic transmitter, which is equipped to insonify directed ultrasonic pulses at an insonification angle β into the test specimen,
   b. An ultrasonic receiver, which is equipped to record echo signals of the ultrasonic pulses insonified into the test specimen,
   c. An actuation and evaluation unit, which is equipped,
      i. To actuate the ultrasonic transmitter of the transmitting test head such that the ultrasonic transmitter is triggered to emit ultrasonic pulses,
      ii. To process the echo signals recorded by the ultrasonic receiver, and
      iii. To determine an ERS value of the flaw from echo signals that can be assigned to a flaw in the volume of the test specimen, wherein
   d. The ultrasonic transmitter comprises a plurality of ultrasonic transducers that can be actuated independently, and
   e. The actuation and evaluation unit is equipped:
      i. To actuate the plurality of ultrasonic transducers individually exactly in phase such that the angle of emission α of the ultrasonic transmitter and thus the insonification angle β in the test specimen can be adjusted electronically,
      ii. To determine the ERS value of a flaw in the volume of the test specimen for a plurality of insonification angles β from echo signals that can be assigned to the flaw, and to generate a B-scan, C-scan or a sector scan as a graphic representation of the flaw, wherein this contains an at least qualitative representation of the dependence of the calculated ERS values of the flaw on the insonification angle β.

15. Device according to claim 14, wherein the actuation and evaluation unit is equipped to automatically compensate for the influence of the electronic adjustment of the insonification angle β on the ERS value of the flaw to be determined in the calculation of the ERS value of the flaw.

16. Device according to claim 14, wherein the device further comprises a path detection unit which is equipped to detect a change in the position of the testing head on the surface of the test specimen.

17. Device according to claim 14, wherein in the scan generated a flaw is symbolized by a bar, the extension of which along its longitudinal axis correlates with the ERS value of the flaw.

18. Device according to claim 14, wherein in the scan generated at least one of the following further characteristics of a flaw is shown:
   a. Relative amplitude of the flaw echo,
   b. Insonification angle β, at which the ERS value of the flaw is at maximum,
   c. Relative flaw size,
   d. Leg from which the flaw echo originates, and
   e. Information on whether the ERS value of the flaw is essentially constant over different insonification angles β.

19. Device according to claim 15, wherein at least one of the following display parameters is used for coding the further flaw characteristics to be represented:
   a. Color,
   b. Dimension of the bar transverse to its longitudinal axis,
   c. Angle of the longitudinal axis of the bar against the surface of the test specimen,
   d. Geometric basic form of the bar.

* * * * *